United States Patent [19]

Berg

[11] Patent Number: 5,705,038

[45] Date of Patent: Jan. 6, 1998

[54] SEPARATION OF PHELLANDRENE FROM LIMONENE BY EXTRACTIVE DISTILLATION

[76] Inventor: Lloyd Berg, 1314 S. Third Ave., Bozeman, Mont. 59715

[21] Appl. No.: 755,640

[22] Filed: Nov. 25, 1996

[51] Int. Cl.$^6$ .................. B01D 3/40; C07C 7/08
[52] U.S. Cl. .................. 203/57; 203/58; 203/59; 203/62; 203/63; 203/64; 203/65; 585/350; 585/865
[58] Field of Search .................. 203/57, 70, 59, 203/58, 64, 63, 62, 65; 585/350, 860, 865, 866

[56] References Cited

U.S. PATENT DOCUMENTS

| | | |
|---|---|---|
| 4,136,126 | 1/1979 | Hirschy et al. .................. 585/355 |
| 4,508,930 | 4/1985 | Wideman et al. .................. 585/377 |
| 5,069,756 | 12/1991 | Berg .................. 203/58 |
| 5,380,405 | 1/1995 | Berg .................. 203/57 |
| 5,391,264 | 2/1995 | Berg .................. 203/57 |
| 5,582,693 | 12/1996 | Berg .................. 203/64 |
| 5,597,455 | 1/1997 | Berg .................. 203/57 |

*Primary Examiner*—Virginia Manoharan

[57] ABSTRACT

Phellandrene is difficult to separate from limonene by conventional distillation or rectification because of the proximity of their boiling points. Phellandreneecan be readily separated from limonene by extractive distillation. Effective agents are o-cresol, tripropylene glycol and isophorone.

1 Claim, No Drawings

SEPARATION OF PHELLANDRENE FROM LIMONENE BY EXTRACTIVE DISTILLATION

FIELD OF THE INVENTION

This invention relates to a method for separating phellandrene from limonene using certain organic compounds as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degrees or more higher than the highest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

The usual method of evaluating the effectiveness of extractive distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility |
|---|---|
| | 1.02  1.1  1.2  1.3  1.4  1.5  2.0  3.0 |
| | Theoretical Stages at Total Reflux |
| 0.999 | 697  144  75  52  40  33  19  12 |
| 0.995 | 534  110  57  39  30  25  14  9 |
| 0.990 | 463  95  49  34  26  22  12  7 |
| 0.98  | 392  81  42  29  22  18  10  6 |
| 0.95  | 295  61  11  21  16  14  8   4 |
| 0.90  | 221  45  23  16  12  10  5   3 |

Phellandrene and limonene boil only three degrees apart and are difficult to separate by conventional distillation or rectification. Table 2 shows that with an agent giving a relative volatility of 1.5, only 30 actual plates are required.

TABLE 2

Theoretical And Actual Plates Required vs. Relative Volatility For Phenllandrene - Limonene Separation

| Relative Volatility | Theoretical Plates Required At Total Reflux, 99% Purity | Actual Plates Required, 75% Eff. |
|---|---|---|
| 1.2  | 49 | 66 |
| 1.35 | 31 | 42 |
| 1.5  | 22 | 30 |

OBJECTIVE OF THE INVENTION

The object of this invention is to provide a process or method of extractive distillation that will enhance the relative volatility of phellandrene from limonene in their separation in a rectification column. It is a further object of this invention to identify effective extractive distillation agents that are stable and can be recycled.

SUMMARY OF THE INVENTION

The objects of this invention are provided by a process for the separation of phellandrene from limonene which entails the use of certain organic compounds when employed as the agent in extractive distillation.

DETAILED DESCRIPTION OF THE INVENTION

I have discovered that certain organic compounds will effectively increase the relative volatility between phellandrene and limonene during rectification when employed as the agent in extractive distillation. Table 3 summarizes the data obtained with these agents. The agents which are effective are o-cresol, isophorone, methyl n-amyl ketoxime, N-methyl pyrrolidinone, 2-methyl-2-,4-pentanediol and tripropylene glycol.

TABLE 3

Effective Extractive Distillation Agents For Separating Phellandrene from Limonene

| Compound | Relative Volatility |
|---|---|
| None | 1.25 |
| o-Cresol | 1.7 |
| Methyl n-amyl ketoxime | 1.45 |
| N-Methyl pyrrolidinone | 1.45 |
| 2-Methyl-2,4-pentanediol | 1.4 |
| Tripropylene glycol | 1.45 |
| Isophorone | 1.35 |

THE USEFULNESS OF THE INVENTION

The usefulness or utility of this invention can be demonstrated by referring to the data presented in Tables 1,2 and 3. All of the successful agents show that phellandrene can be separated from limonene by means of extractive distillation and that the ease of separation is considerable.

WORKING EXAMPLE

Example 1

Fifty grams of a phellandrene—limonene mixture and fifty grams of o-cresol as the extractive distillation agent were charged to a vapor-liquid equilibrium still and refluxed for three hours. The vapor composition was 49.1% phellandrene and 50.9% limonene; the liquid composition was 36.2% phellandrene and 63.8% limonene. This is a relative volatility of 1.7.

I claim:

1. A method for recovering phellandrene from a mixture consisting of phellandrene and limonene which consists essentially of distilling said mixture consisting of phellandrene and limonene in the presence of an extractive distillation agent, recovering the phellandrene as overhead product and obtaining the limonene and the extractive distillation agent as bottoms product, wherein said extractive distillation agent consists of one material selected from the group consisting of o-cresol, methyl n-amyl ketoxime, N-methyl pyrrolidinone, tripropylene glycol, 2-methyl-2,4-pentanediol and isophorone.

* * * * *